United States Patent

Westphal et al.

[11] Patent Number: 5,863,179
[45] Date of Patent: *Jan. 26, 1999

[54] CENTRIFUGAL BLOOD PUMP

[75] Inventors: Dieter Westphal, Woerthsee; Helmut Reul, Duren; Guenter Rau, Aachen, all of Germany

[73] Assignee: Baxter International Inc., Deerfield, Ill.

[*] Notice: The term of this patent shall not extend beyond the expiration date of Pat. No. 5,746,575.

[21] Appl. No.: 963,591

[22] Filed: Nov. 3, 1997

Related U.S. Application Data

[63] Continuation of Ser. No. 569,098, filed as PCT/EP94/02049 Jun. 23, 1994, Pat. No. 5,746,575.

[30] Foreign Application Priority Data

Jun. 25, 1993 [DE] Germany ............................ 43 21 260.3

[51] Int. Cl.⁶ ...................................................... F04D 29/04
[52] U.S. Cl. ........................................... 415/206; 415/900
[58] Field of Search .................................... 415/206, 900; 417/423.12, 424.1

[56] References Cited

U.S. PATENT DOCUMENTS

| 4,065,234 | 12/1977 | Yoshiyuki et al. . |
| 4,253,798 | 3/1981 | Sugiura . |
| 4,507,048 | 3/1985 | Belenger et al. . |
| 4,589,822 | 5/1986 | Clausen et al. . |
| 4,984,972 | 1/1991 | Clausen et al. . |
| 5,017,103 | 5/1991 | Dahl . |
| 5,147,187 | 9/1992 | Ito et al. . |
| 5,322,413 | 6/1994 | Vescovini et al. . |
| 5,360,317 | 11/1994 | Clausen et al. . |
| 5,399,074 | 3/1995 | Nosé . |
| 5,458,459 | 10/1995 | Hubbard et al. . |

FOREIGN PATENT DOCUMENTS 0 451 376   10/1991   European Pat. Off. .

*Primary Examiner*—John T. Kwon
*Attorney, Agent, or Firm*—Guy L. Cumberbatch; Debra D. Condino

[57] ABSTRACT

A magnetically-driven centrifugal blood pump includes a housing and an impeller mounted for rotation within. The impeller includes a generally disk-shaped base plate and a plurality of curvilinear vanes extending axially upward therefrom. The vanes project radially outward from the base plate approximately one-third of their curvilinear length. The housing includes a rear wall spaced from the impeller base plate across a constant gap, with a sloped transition wall surrounding the rear wall and joining it to a peripheral wall. A tangential outlet is provided in the peripheral wall. A front wall extends inward from the peripheral wall with a slight conicity to an axial inlet. The vanes each have a front edge which slopes away from the front wall in the radially outward direction to provide a widening gap therebetween. The vanes have inner ends which together define a vane-free inner region below and slightly larger than the inlet. The curvature of each vane changes along its length, and a tangent angle progresses from the inner end to the outer end according to a preferred formula. Desirably, the impeller includes a pair of low magnetic retentivity plates, such as steel, which are driven by an external drive which sets up a rotating magnetic field.

49 Claims, 3 Drawing Sheets

CENTRIFUGAL BLOOD PUMP

This is a continuation of application Ser. No. 08/569,098, filed as PCT/EP94/02049 Jun. 23, 1994, now U.S. Pat. No. 5,746,575.

FIELD OF THE INVENTION

The invention relates to a blood pump which is configured as a centrifugal pump, comprising an impeller rotating in a pump housing.

BACKGROUND OF THE INVENTION

A blood pump disclosed in U.S. Pat. No. 4,507,048 comprises an impeller being supported in the pump housing between two tip bearings, the blades of the impeller being arranged at the front of a central cone. On the back side of the central cone, there is a plate having a constant distance from the back wall of the pump housing. The profiling of the blades is similar to that of aircraft wings, and they have an angle of contact of about 15°. The blades are covered by a cone envelope in which another cone envelope is arranged so that the impeller forms an altogether rotating partially hollow body wherein the blades are arranged.

From EP 0 451 376 A1, a blood pump is known wherein the impeller comprises a plane plate from which the blades project to the front, towards the inlet. The blades are slightly bent and their height decreases linearly outward. The impeller is attached to a shaft one end of which is supported in an extension of the pump housing. The front wall of the pump housing has a truncated configuration, and, with increasing radius, the back wall is set back.

Further, a blood pump is known from U.S. Pat. No. 4,589,822, wherein the impeller is fastened to a shaft which is also supported outside the pump housing. The impeller comprises linear blades whose height decreases linearly outwards. The front wall of the pump housing has a truncated configuration and, with the radius increasing, the back wall is set back. The blades only have an angle of contact of about 60°. Outwards, they project beyond the plate.

From U.S. Pat. No. 4,984,972, a blood pump is known in which an impeller consisting of a plate with a plane upper surface and a conically extending lower surface is oscillatingly supported on a tip bearing. The height of the blades of the impeller linearly decreases radially outward, the blades terminating at the outer plate edge.

Centrifugal pumps for industrial applications are configured such that they have a high pump rate with low delivery pressure. On the contrary, blood pumps have to be configured for low pump rates and relatively high pressures. A problem with blood pumps is that they are subject to considerably varying operational conditions and that it has to be ensured that harm to blood is avoided. A blood pump, for example, is used for taking over the pump function of the heart of a patient during an operation. When a vasodilative medicine is administered to the patient, the fluid resistance of the patient body decreases and the pressure against which the blood pump has to feed decreases. Further, blood pumps can be used for fully taking over the heart function or for exerting a heart-supporting function only. Accordingly, a blood pump has to be capable of delivering varying quantities (by means of different speeds). Furthermore, a blood pump has to be configured such that it operates in the occurring wide application ranges with minimum blood disintegration. Blood disintegration happens, e.g., by local temperature rises of the blood pump in the support region of the impeller, but particularly by transverse stresses and shearing stresses to which the blood is exposed in the centrifugal pump. Such effects cause a disintegration of the blood due to hemolysis, thrombocytes being activated and aggregating. This may lead to perilous clot formations. Clot formations also form in dead water zones of insufficient flow through the pump housing.

An optimization of the flow conditions in blood pumps with the target to avoid any harm to blood cannot be achieved at present on the basis of calculations and theoretical considerations due to the various operational conditions to which a blood pump may be exposed. When designing a blood pump, the engineer is dependent, to a great extent, on empiric research.

SUMMARY OF THE INVENTION

It is the object of the invention to provide a blood pump which operates with minimum blood disintegration and which has a simple construction so that it can be manufactured as a disposable article at low cost.

The object is solved, according to the invention, by a centrifugal blood pump having a rigid housing with an axial inlet and an outlet on the periphery. The housing includes a radially disposed front wall adjacent and surrounding the inlet, a peripheral wall connected to the front wall defining the outer boundary of a pumping chamber, the outlet opening from the peripheral wall. A transition wall connects to the peripheral wall and slopes therefrom radially inward and away from the front wall. A radially disposed rear wall connects to the transition wall. An impeller is mounted for axial rotation within the pumping chamber and comprises ferromagnetic coupling members. Impeller vanes project axially from a base plate toward the inlet, each of the vanes including a front edge sloping away from the front wall from an inner end to an outer end. The base plate is spaced a substantially constant distance from the rear wall of the housing.

In the blood pump according to the invention, the impeller is supported between axial sliding bearings within the pump housing, whereby complex rolling bearings and shaft seals are omitted. Thereby, friction is held on a low level so that a frictional heating is practically eliminated. The terms axial sliding bearings includes tip bearings and also particularly a thrust ball bearing with a ball arranged along the rotational axis. The impeller comprises blades which freely project from a plate and are not encompassed by a cover. The individual blades have a very high angle of contact of 90°–120°, preferably of about 110°. Due to the high angle of contact, the blood pump is capable of delivering the required high pressure and, on the other hand, of performing the increase in pressure continuously and with low transverse stresses.

With the radius increasing, the height of the blades decreases linearly outwards, while the front wall of the pump housing extends substantially parallel to the plate of the impeller but has a small conicity of about 3° to 10°, so that air bubbles can escape to the inlet when the pump stands in a vertical position. Thereby, the distance between the blades and the front wall of the housing increases linearly so that the gap formed between the blades and the front wall of the housing linearly increases with the radius. Since the circumferential speed also increases with the radius, the shearing rate at the front side of the impeller is substantially constant. This means that the normally appearing shearing stress peaks are avoided. The gap formed between the plate and the back wall of the pump housing is constant at the back side of the plate. The gap width should be greater than 1 mm, preferably about 2 mm. Thereby, secondary flows are produced at the back side of the impeller, whereby the blood continuously circulates so that the formation of dead water zones is not possible.

The blades begin only relatively far at the outside on the impeller, i.e. the blade-free central region has a relatively large diameter with respect to the outer diameter of the impeller. The blade leading angle only amounts to 18°–25°. This small leading angle prevents shearing stress peaks in the very critical inlet area. The blade trailing angle is also much smaller than is common in centrifugal pumps of this size.

BRIEF DESCRIPTION OF THE DRAWINGS

Hereinafter, an embodiment of the invention is described in detail with reference to the drawings, in which.

DESCRIPTION OF THE PREFERRED EMBODIMENTS(S)

Figure 1:
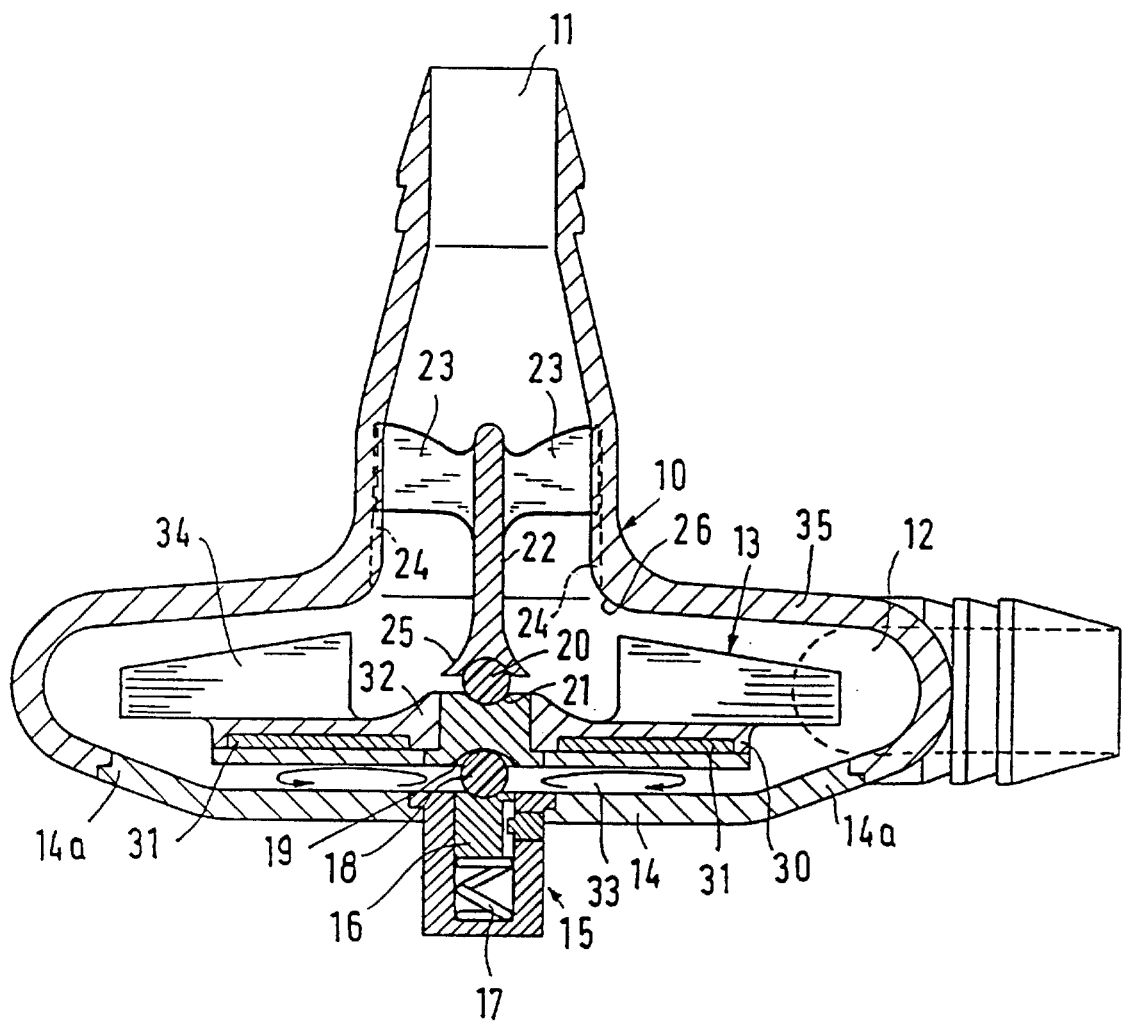
FIG. 1 is a longitudinal section through the blood pump.

The blood pump comprises a round flat (plate-shaped) pump housing 10 having a diameter of about 60 mm which is provided with an inlet 11 along its axis. The outlet 12 is tangentially arranged on the periphery of the pump housing 10.

In the pump housing 10, the impeller 13 is supported by means of an axial sliding bearing. In the back wall 14 of the pump housing, there is a supporting device 15 for a ball holder 16. The supporting device 15 includes a spring 17 which presses the ball holder 16 against the impeller 13. Along the axis of the impeller, a ceramic ball 18 is adhered to the ball holder 16. This ball 18 projects into a ball cup 19 of the impeller 13, the diameter of the ball cup 19 being generally twice as large as the diameter of the ball 18.

Another ceramic ball 20 arranged on the impeller axis and projecting into a ball cup 21 which is opposed to the ball cup 19 serves as abutment for the ball 18. The ball 20 is adhered to a ball holder 22 which projects into the tubular inlet 11 and is provided with laterally projecting ribs 23 protruding into longitudinal grooves 24 of the tubular wall of the inlet 11. In the two spherical thrust bearings, the ratio $R_{spherical\ cap}/R_{ball}$ is between 1.5/1 and 3/1 so that the ball has only point contact with the associated spherical cap. Ball and spherical cap consist of a material combination providing favorable friction conditions, e.g. steel—ceramic or ceramic—ceramic.

The free end 25 of the ball holder 22 is expanded in a trumpet-like manner, the expansion having a radius of about 5 mm. This expansion serves to radially divert the blood coming from the inlet 11 to the impeller. The transition 26 from the inlet 11 to the pump room of the pump housing has a radius of curvature of about 3 mm. The transition from the axial flow in the inlet 11 to the rotational flow in the pump room is made without any abrupt change of cross section. The inlet region of the impeller, which is strongly influenced by the flow diversion of 90°, is particularly favorable to flow and configured so as to treat the blood carefully. This is achieved by the fact that at the transition of the inlet 11 to the pump room, the flow cross section increases by about the factor 6 (from 140 mm² in the inlet connection piece to 850 mm² at the blade beginning), with the diversion radii being particularly large there.

The impeller 13 comprises a plane plate 30 in which ferromagnetic plates 31 are embedded. In its central portion 32 at the side facing the inlet 11, the plate 30 is configured so as to be thickened by less than the plate thickness. This thickening in the central portion 32 is rounded, the radius corresponding to that of the trumpet-shaped region 25. The central portion 32 is free of blades. Its radius R1 is 9 mm and is slightly larger than the radius of the inlet 11 at the transition into the pump chamber. The radius R2 of the impeller is 24 mm and the radius R3 of the plate 30 is 18 mm.

A gap 33 of constant width of about 2 mm is formed between the back side of the plate 30 and the back wall 14. Upon rotation of the impeller 13, secondary flows, as indicated by the arrows, are formed in the gap 33. These secondary flows prevent the formation of dead water zones in the gap 33.

The impeller 13 comprises four to seven (here: five) blades 34 which begin at the periphery of the central portion 32 and radially project beyond the plate 30 by about one third of the blade length. In the region of the projecting lengths of the blades 34, the back wall 14 is provided with a sloping portion 14a in order to compensate for the lack of plate 30 in the outer region of the pump chamber. Thus, the width of the pump chamber reduces towards the outer edge and towards outlet 12.

The front wall 35 of the pump chamber extends approximately parallel to the central portion of the back wall 14 and the plate 30. The blades 34 have their greatest height at the inner end, i.e. at the periphery of the central portion 32. The blade height decreases linearly outwards to about half. The gap between the front wall 35 of the pump housing and the blade edges widens radially outwards. Since the circumferential speed of the blood also increases radially outwards, the shearing rate remains constant.

Figure 2:
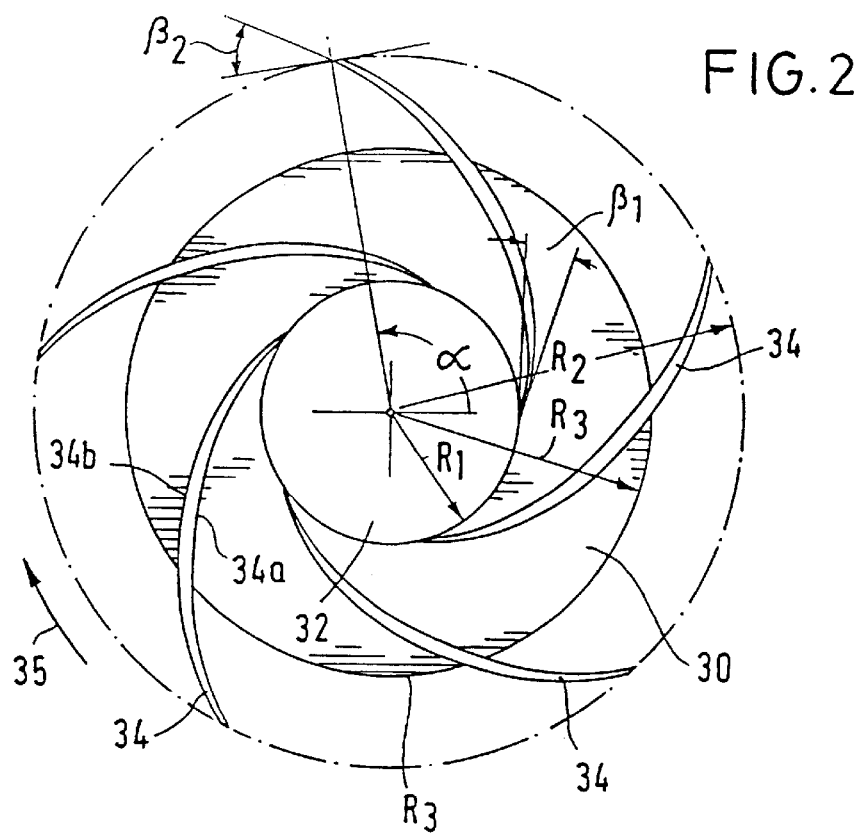
FIG. 2 is a plan view of the impeller.

As shown in FIG. 2, each blade 34 is curved in an arc-like manner in the rotational direction 35, the angle of contact a of one blade being 100°. The blade leading angle β1, namely the tangent angle of the blade at the central portion 32, amounts to 20° and the blade trailing angle β2, namely the tangent angle of the blade at the circle having the radius R2 and encompassing the blade ends, amounts to 30°. The concave inner side 34a of the blade forms the suction side and the convex outer side 34b forms the pressure side. The blades have their smallest thickness at the leading end and the trailing end. For reasons of stability, the blade thickness increases towards the center, the blade having the greatest thickness in the central portion. The blade is rounded at the leading end.

Figure 3:
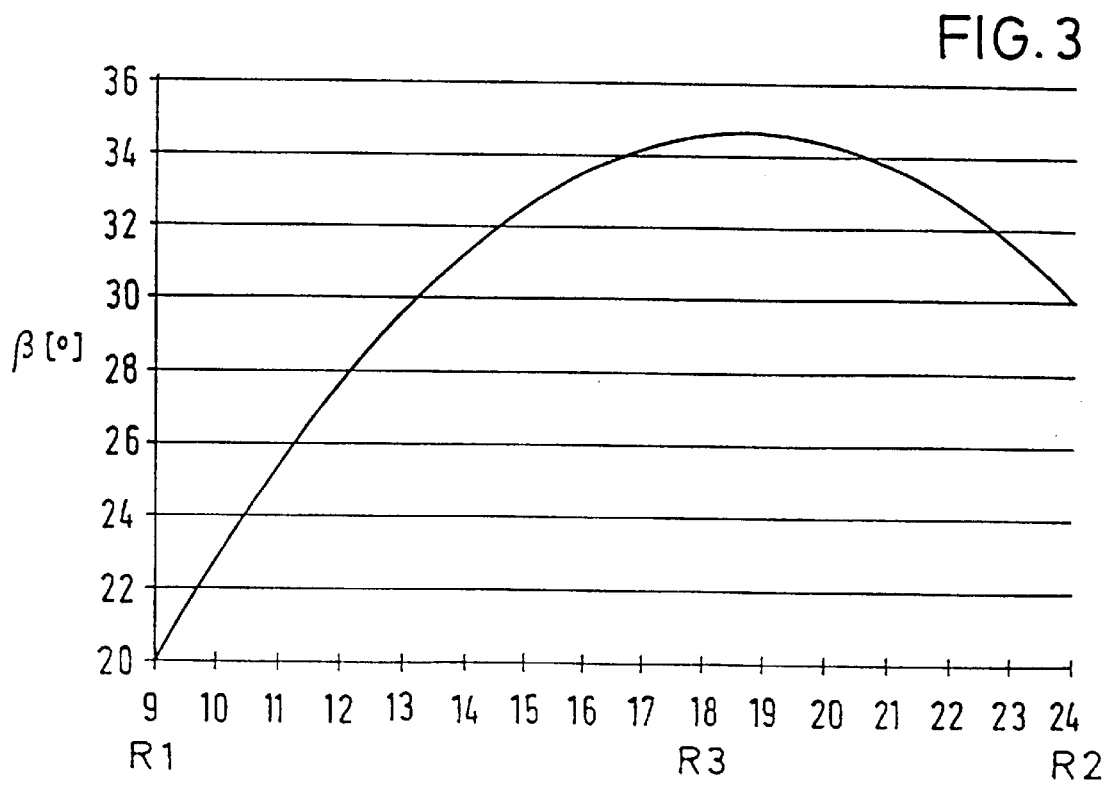
FIG. 3 is a graph showing the progression of the blade angle β as a function of the radius r.

FIG. 3 shows the progression of the tangent angle β of the blade as a function of the radius r. The course β(r) corresponds to a polynomial of the second degree:

$$\beta(r)=Ar^2+Br+C.$$

A, B, and C are constants. In the present embodiment, A=−0.16; B=5.95; C=−20.56.

The described structural shape of pump housing and impeller permits an essentially smaller filling volume than is the case with other blood pumps of the same pump capacity. The filing volume here only amounts to 30 ml (milliliters).

Owing to the small filling volume, the extracorporeal blood volume is readuced and the contact of the blood with foreign surfaces, which considerably contributes to harming the blood, is reduced. The blood pump can be manufactured of a small number of parts at low cost. For medical reasons, it is provided for being used only once.

Figure 4:
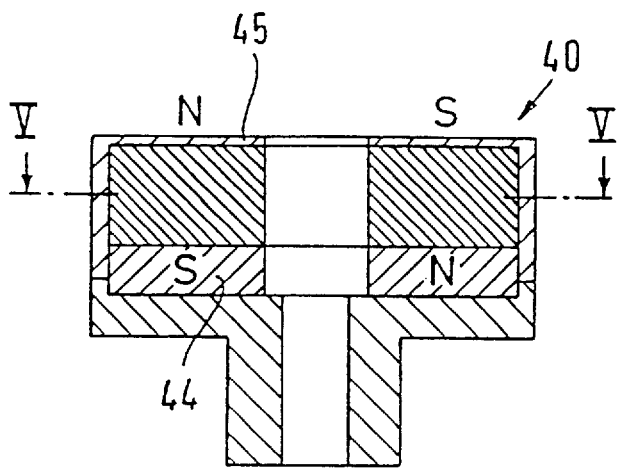
FIG. 4 is a longitudinal section through the driving wheel.
Figure 5:
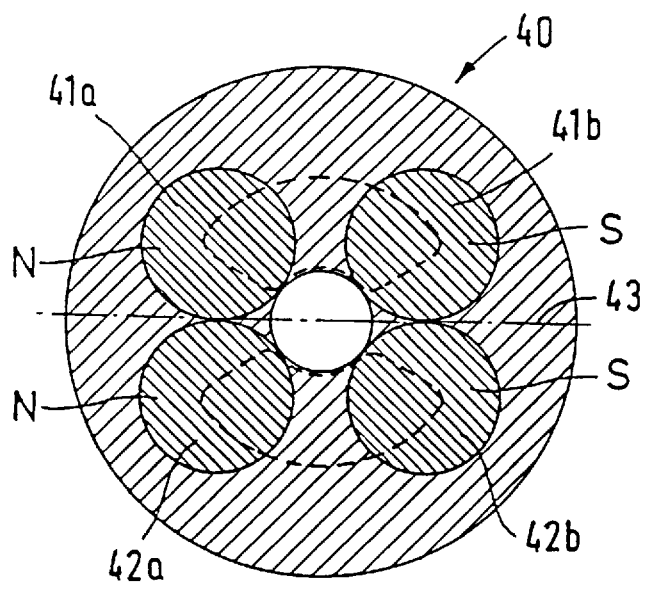
FIG. 5 is a section along line V—V of FIG. 4.
Figure 6:
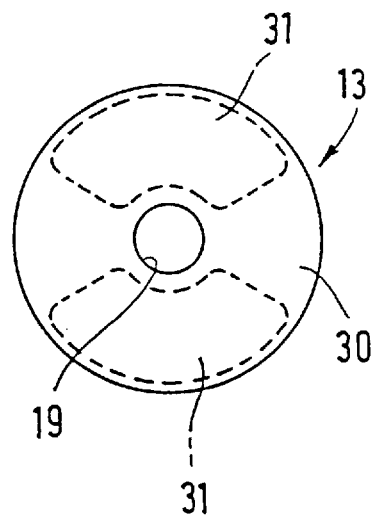
FIG. 6 is a schematic view showing the magnetically low retentivity plates in the impeller.

The described blood pump is used in combination with the driving wheel 40 illustrated in FIGS. 4 and 5. This driving wheel comprises two pairs of bar magnets 41*a,* 41*b;* 42*a,* 42*b,* each pair being arranged on a different side of the radius 43 of the driving wheel. In the drawings, the polarities of the bar magnets are indicated with N (north pole) and S (south pole). The back sides of the bar magnets are in contact with a ferromagnetic plate 44 which forms the pole backflow path. The front side 45 of the bar magnets has a magnetic effect on the ferromagnetic plates 31 through the wall of the pump housing 10, said plates closing the magnetic flux on the front side of the bar magnets. The driving wheel 40 is driven by a motor and thus pulls along the disc 30 supported in the pump housing 10. The plates 31 included in the disc 30 only consists of magnetically low retentivity (ferromagnetic) material, e.g. of simple constructional steel. Each of them has a circumferential extension of 120° and a thickness of 1 mm.

When the pump is driven with a speed of 3,000 rpm, it delivers a quantity of 4 l/min (liters per minute) with a delivery pressure of 180 mmHg.

We claim:

1. A centrifugal blood pump, comprising:

a rigid housing having an axial inlet opening to a wider pumping chamber formed generally symmetrically about an axis, and a tangential outlet from the pumping chamber;

the pumping chamber including a generally radially disposed front wall adjacent and surrounding the inlet, a peripheral wall connected to the front wall defining the outer boundary of the pumping chamber, the tangential outlet opening from the peripheral wall, a transition wall connected to the peripheral wall and sloped therefrom radially inward and away from the front wall, and a radially disposed rear wall connected to the transition wall; and an impeller mounted for axial rotation within the pumping chamber, the impeller having a circular base plate parallel to and axially spaced from the rear wall, the base plate having a diameter approximately equal to the diameter of the rear wall, the impeller further including a plurality of curvilinear vanes projecting axially upward from the base plate, each of the vanes having a radially inner end spaced from the axis of the pumping chamber to define collectively therebetween a void, each of the vanes having a rear edge connected to the base plate and continuing radially outwardly therefrom toward the peripheral wall to terminating in outer ends, each vane further including a front edge sloping away from the front wall from the inner end to the outer end.

2. The pump of claim 1, wherein the vanes are curved and have a length, the vanes extending outward from the plate approximately one-third of their length.

3. The pump of claim 1, wherein the axial height of each vane decreases by approximately half from the inner end to the outer end.

4. The pump of claim 3, wherein the front wall has a slight conicity of between about 3° to 10°.

5. The pump of claim 1, wherein the outer ends of the vanes define a circle with a first diameter, and at least some of the inner ends are equidistantly spaced from the axis so that a circular vane-free region is formed therewithin having a second diameter, the ratio of the second diameter to the first diameter being between about 0.25 to 0.5.

6. The pump of claim 5, wherein the ratio is about 0.375.

7. The pump of claim 5, wherein the inlet is formed centrally in the front wall and opens to the pumping chamber with a third diameter, and wherein the second diameter is greater than the third diameter.

8. The pump of claim 1, wherein an angle of contact of each vane is defined by an included angle between radial vectors through the inner and outer ends, and the angle of contact is between about 90° to 120°.

9. The pump of claim 8, wherein the angle of contact is about 100°.

10. The pump of claim 1, wherein the inner end of each vane forms a leading angle with respect to a tangent to a circular vane-free region defined by the inner ends of at least some of the vanes, and the outer end of each vane forms a trailing angle with respect to a tangent to the circle defined by the vane outer ends, the trailing angle being greater than the leading angle.

11. The pump of claim 10, wherein the trailing angle is between about 25° to 40°.

12. The pump of claim 11, wherein the trailing angle is about 30°.

13. The pump of claim 1, wherein the thickness of each vane increases from the inner and outer ends towards the middle of the blade.

14. The pump of claim 1, wherein the centrifugal pump is magnetically driven and includes a plurality of planar members of low magnetic retentivity embedded in the base plate adapted to be driven by an external magnetically-coupled drive.

15. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, the vanes extending radially outward from the plate toward the peripheral wall, wherein the rear wall further includes an annular portion surrounding the central portion and sloped toward the front wall from the central portion to the peripheral wall.

16. The pump of claim 15, wherein the vanes are curved and have a length, the vanes extending outward from the plate approximately one-third of their length.

17. The pump of claim 15, wherein the centrifugal pump is magnetically driven and includes a plurality of planar members of low magnetic retentivity embedded in the base plate adapted to be driven by an external magnetically-coupled drive.

18. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, the vanes extending radially outward from the plate toward the peripheral wall, wherein the vanes each include an inner end and an outer end, and a front edge which forms a front gap with the front wall, the front gap diverging from the inner end to the outer end to reduce the difference in sheer stresses imposed on the blood at the inner and outer ends, respectively.

19. The pump of claim 18, wherein each vane has an axial height which decreases from the inner end to the outer end.

20. The pump of claim 19, wherein the axial height of each vane decreases by approximately half from the inner end to the outer end.

21. The pump of claim 19, wherein the front wall has a slight conicity of between about 3° to 10°.

22. The pump of claim 18, wherein the centrifugal pump is magnetically driven and includes a plurality of planar members of low magnetic retentivity embedded in the base plate adapted to be driven by an external magnetically-coupled drive.

23. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, the vanes extending radially outward from the plate toward the peripheral wall, wherein the vanes each include an inner end and an outer end, the outer ends of the vanes defining a circle with a first diameter, and at least some of the inner ends are equidistantly spaced from the axis to define a circular vane-free region therewithin having a second diameter, the ratio of the second diameter to the first diameter being between about 0.25 to 0.5.

24. The pump of claim 23, wherein the ratio is about 0.375.

25. The pump of claim 23, wherein the inlet is formed centrally in the front wall and opens to the pumping chamber with a third diameter, and wherein the second diameter is greater than the third diameter.

26. The pump of claim 23, wherein the vanes are curved.

27. The pump of claim 23, wherein the centrifugal pump is magnetically driven and includes a plurality of planar members of low magnetic retentivity embedded in the base plate adapted to be driven by an external magnetically-coupled drive.

28. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, the vanes extending radially outward from the plate toward the peripheral wall, wherein the vanes are curved and each includes an inner end and an outer end, and wherein an angle of contact of each vane is defined by an included angle between radial vectors through the inner and outer ends, and the angle of contact is between about 90° to 120°.

29. The pump of claim 28, wherein the angle of contact is about 100°.

30. The pump of claim 28, wherein the inner end of each vane forms a leading angle with respect to a tangent to a circular vane-free region defined by the inner ends of at least some of the vanes, and the outer end of each vane forms a trailing angle with respect to a tangent to the circle defined by the vane outer ends, the trailing angle being greater than the leading angle.

31. The pump of claim 30, wherein the trailing angle is between about 25° to 40°.

32. The pump of claim 31, wherein the trailing angle is about 30°.

33. The pump of claim 28, wherein the centrifugal pump is magnetically driven and includes a plurality of planar members of low magnetic retentivity embedded in the base plate adapted to be driven by an external magnetically-coupled drive.

34. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, each vane has an inner end and extends radially outward from the plate toward the peripheral wall to terminate in an outer end, wherein the inner end of each vane forms a leading angle with respect to a tangent to a circular vane-free region defined by the inner ends of at least some of the vanes, and the outer end of each vane forms a trailing angle with respect to a tangent to the circle defined by the vane outer ends, the trailing angle being greater than the leading angle.

35. The pump of claim 34, wherein the trailing angle is between about 25° to 40°.

36. The pump of claim 35, wherein the trailing angle is about 30°.

37. The pump of claim 34, wherein a tangent angle of each vane increases from the leading angle to a maximum angle at a point between the inner and outer ends, and decreases from the maximum angle to the trailing angle.

38. The pump of claim 37, wherein the tangent angle $\beta$ along each vane is defined by the formula:

$$\beta(r)=Ar^2+Br+C,$$

where r is the radial distance from the axis, A is negative, B is positive, and C is negative.

39. The pump of claim 34, wherein an angle of contact of each vane is defined by an included angle between radial vectors through the inner and outer ends, and the angle of contact is between about 90° to 120°.

40. The pump of claim 34, wherein the thickness of each vane increases from the inner and outer ends towards the middle of the blade.

41. The pump of claim 34, wherein the centrifugal pump is magnetically driven and includes a plurality of planar members of low magnetic retentivity embedded in the base plate adapted to be driven by an external magnetically-coupled drive.

42. A centrifugal blood pump, comprising:

an outer housing defining a pumping chamber within, the pumping chamber being generally symmetric about a central axis, the housing having a front wall, a rear wall axially spaced from the front wall, and a peripheral wall connecting the front and rear walls;

an inlet in the front wall;

an outlet in the peripheral wall;

an impeller mounted for axial rotation in the pumping chamber and comprising a planar plate axially spaced from a central portion of the rear wall across a rear gap of substantially constant dimension, the impeller further including a plurality of vanes axially projecting from the plate toward the front wall, each vane has an inner end and extends radially outward from the plate toward the peripheral wall to terminate in an outer end, wherein the vanes are curved and have a curvilinear length, the vanes extending outward from the plate approximately one-third of their length.

43. The pump of claim 42, wherein the outer ends of the vanes defining a circle with a first diameter, and at least some of the inner ends are equidistantly spaced from the axis so that a circular vane-free region is formed therewithin having a second diameter, the ratio of the second diameter to the first diameter being between about 0.25 to 0.5.

44. The pump of claim 43, wherein the inner end of each vane forms a leading angle with respect to a tangent to a circular vane-free region defined by the inner ends of at least some of the vanes, and the outer end of each vane forms a trailing angle with respect to a tangent to the circle defined by the vane outer ends, the trailing angle being greater than the leading angle.

45. The pump of claim 44, wherein the trailing angle is between about 25° to 40°.

46. The pump of claim 42, wherein an angle of contact of each vane is defined by an included angle between radial vectors through the inner and outer ends, and the angle of contact is between about 90° to 120°.

47. The pump of claim 42, wherein the vanes each include a front edge which forms a front gap with the front wall, the front gap diverging from the inner end to the outer end to reduce the difference in sheer stresses imposed on the blood at the inner and outer ends, respectively.

48. The pump of claim 47, wherein each vane has an axial height which decreases from the inner end to the outer end.

49. The pump of claim 42, wherein the centrifugal pump is magnetically driven and includes a plurality of planar members of low magnetic retentivity embedded in the base plate adapted to be driven by an external magnetically-coupled drive.

* * * * *